(12) United States Patent
Martin et al.

(10) Patent No.: US 6,653,533 B1
(45) Date of Patent: Nov. 25, 2003

(54) NUCLEIC ACIDS ENCODING PROTEINS WITH PATHOGEN RESISTANCE ACTIVITY AND PLANTS TRANSFORMED THEREWITH

(75) Inventors: Gregory B Martin, Ithaca, NY (US); Jian-Min Zhou, Manhattan, KS (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/202,161

(22) PCT Filed: Jun. 12, 1997

(86) PCT No.: PCT/US97/10382

§ 371 (c)(1),
(2), (4) Date: Jun. 14, 1999

(87) PCT Pub. No.: WO97/47183

PCT Pub. Date: Dec. 18, 1997

Related U.S. Application Data

(60) Provisional application No. 60/046,494, filed on May 14, 1997, and provisional application No. 60/019,633, filed on Jun. 12, 1996.

(51) Int. Cl.$^7$ .............................. A01H 5/00; C12N 5/14; C12N 15/82
(52) U.S. Cl. ...................... 800/301; 435/419; 435/468; 800/279; 800/298
(58) Field of Search .................. 435/69.1, 352.3, 435/352.33, 252.34, 254.2, 320.1, 419, 468, 471; 536/23.6; 800/278, 279, 298, 301

(56) References Cited

U.S. PATENT DOCUMENTS 5,648,599 A   7/1997   Tanksley et al. ............ 800/205

OTHER PUBLICATIONS

Zhou, JianMin; Tang, Xiaoyan; Martin, Gregory B., *Involvement of Transcription Factors in the PTO–Signaling Pathway*, Abstract submitted to the Organizers of the 8$^{th}$ International Congress on Molecular Plant–Microbe Interactions (Mar. 20, 1996). Congress held Jul. 14–19, 1996.

Koziel, Michael G.; Carozzi, Nadine B.; and Desai, Nalini, *Optimizing expression of transgenes with an emphasis on post–transcriptional events*, Plant Molecular Biology, vol. 32, pp. 393–405, 1996. ©1996 Kluwer Academic Publishers. Printed in Belgium.

Stam, Maike; Mol, Joseph N.M.; and Kooter, Jan M., *The Silence of Genes in Transgenic Plants*, Annals of Botany 79, pp. 3–12, 1997.

Smith, C.J.S.; Watson, C.F.; Ray, J.; Bird, C.R.; Morris, P.C., Schuch, W. and Grierson, D., *Antisense RNA inhibition of polygalacturonase gene expression in transgenic tomatoes*, Nature, vol. 334, pp. 724–726, Aug. 25, 1988.

Ohme–Takagi, Masaru and Shinshi, Hideaki; *Ethylene–Inducible DNA Binding proteins That Interact with an Ethylene–Responsive Element*, The Plant Cell, vol. 7, pp. 173–182, Feb. 1995. ©American Society of Plant Physiologists.

Zhou, Jianmin; Tang, Xiaoyan and Martin, Gregory B.; *The Pto kinase conferring resistance to tomato bacterial speck disease interacts with proteins that bind a cis–element of pathogenesis–related genes*, The EMBO Journal, vol. 16, No. 11, pp. 3207–3218, Jun. 2, 1997 ©Oxford University Press.

Zhou, Jianmin; Bressan, Ray A.; and Martin, Gregory B., *The Tomato Gene Pti1 Encodes a Serine/Threonine Kinase That Is Phosphorylated by Pto and Is Involved In the Hypersensitive Response*, Cell, vol. 83, pp. 925–935, Dec. 15, 1995. ©1995 by Cell Press.

Tobias, C.M.: *A kinase suicide squad in tomato*, Trends Plant Scie., (1996) vol. 1, No. 5, pp. 133–134.

Primary Examiner—Amy J. Nelson
(74) Attorney, Agent, or Firm—Woodard, Emhardt, Moriarty, McNett & Henry LLP

(57) ABSTRACT

The present invention relates to methods and materials for the protection of plants against pathogens through plant genetic engineering, and more particularly to genes which enhance disease resistance in plants by encoding proteins that physically interact with R gene products involved in activation of plant defense mechanisms. The invention further relates to three nucleotide sequences which have been cloned, isolated and sequenced, three amino acid sequences encoded thereby and a transgenic plant and methods for making the same, the genome of the plant having incorporated therein a foreign nucleotide sequence selected in accordance with the invention which functions to enhance the plant's ability to resist pathogens.

42 Claims, 4 Drawing Sheets

```
Pti4  ..............MDQ....QLPPTNFPVDFPVYRRNSSFSRLIPCLTEK
Pti5  ...........................................LVP...TP
Pti6  ..........................................MTENSVPVIKFT

"B"
Pti4  WGDLPLKVD........DSE.DMVIYGLLKD..ALSVGW........SPF
Pti5  QSDLPLNEN........DSQ.EMVLYEVLNEANALNIPY........LP.
Pti6  QHIVTTNKHVFSEHNEKSNSELQRVVRIILTDADAIDSS............

"A"
Pti4  NFTAGEVKSEPREEIESSPEF.....SPS...PAGTTAAPAAETPKRRHYR
Pti5  .........QRNQLLPRNNI.....LRPLQ............CIGKKYR
Pti6  ...DDEGRNTVRRVKRHVTEINLMPSTKSIGDRKRRSVSPDSDVTRRKKFR

Pti4  GVRQRPWGKFAAEIRDPAKNGARVWLGTYETAEEAAIAYDKAAYRMRGSKA
Pti5  GVRRRPWGKYAAEIRDSARHGARVWLGTYETAEEAALAYDRAAFRMRGAKA
Pti6  GVRQRPWGRWAAEIRDPTR.GKRVWLGTYDTPEEAAVVYDKAAVKLKGPDA

Pti4  HLNFPHRIG.LNEPEPFELRRKGRAIQGPASSS...GNGSMKRRRKAV..Q
Pti5  LLNFPSEI..........VNASVSVDKLSLCSNSYTTNNNSDSSLNEVSSG
Pti6  VTNFP.....VSTTAEVTVTVTETETESVADGGDKSENDVALSPTSVLCDN

Pti4  KCDG.EMASRSS..VMQVGCQIEQLTGVHQLLVI*................
Pti5  TNDVFESRC*........................................
Pti6  DFAPFDNLGFCE..VDAFGFDVDSLFRLPDFAMTEKYYGDEFGEFDFDDFA

Pti4  ..................................................
Pti5  ..................................................
Pti6  LEAR*.............................................
```

NUCLEIC ACIDS ENCODING PROTEINS WITH PATHOGEN RESISTANCE ACTIVITY AND PLANTS TRANSFORMED THEREWITH

REFERENCES TO RELATED APPLICATIONS

This application claims the benefit of U.S. Provisional Application No. 60/019,633, filed Jun. 12, 1996 and U.S. Provisional Application No. 60/046,494, filed May 14, 1997, each of which is hereby incorporated by reference herein in its entirety.

This invention was made with government support under the following grant: grant number MCB-96-30635 awarded by NSF. The government has certain rights in the invention.

BACKGROUND OF THE INVENTION

1. Field of the Invention

The present invention relates to methods and materials for the protection of plants against pathogens through plant genetic engineering. More particularly, the invention relates to genes which enhance a plant's ability to withstand pathogen attack by encoding proteins that physically interact with proteins encoded by disease resistance genes (R genes) in a plant's signal transduction pathway to activate plant defense mechanisms. The invention also relates to transgenic plants and methods for making the same, the genomes of the plants having incorporated therein foreign nucleotide sequences selected in accordance with the invention which function to enhance the plants ability to resist pathogens.

2. Discussion of Related Art

Crop losses resulting from pathogenic organisms such as viruses, bacteria, fungi and nematodes is a historic and widespread problem in a wide variety of agricultural industries. These crop losses caused by pathogen-related plant damage result in economic losses amounting to billions of dollars annually. This problem has been addressed in the past by employing a wide variety of chemicals to reduce pest damage to plant crops. The approach, however, has been associated with many environmental problems created by the widespread use of pesticidal chemicals, and the chemicals often only provide a transient level of protection for crops. Chemicals also suffer from the disadvantage that all organisms in an area may be indiscriminately treated, causing needless damage to many beneficial organisms. Perhaps more importantly, many chemicals are potentially toxic to man and animals and often become concentrated in, for example, lakes and ponds and/or other water supplies.

As a result, alternate methods have been explored to reduce crop damage, one example being selective breeding of plants based upon pathogen resistance characteristics. Resistance traits, however, are sometimes controlled by many genes, making it difficult to genetically select a desired attribute to a satsfactory degree. Decreased crop yields are also occasionally encountered in resistant plants developed by selective breeding. Accordingly, there exists a strong need for compositions and methods to improve the resistance of plants from attack by pathogens. Such are provided by the present invention, which provides compositions and methods useful for genetically transforming a plant and thereby enhancing the plant's resistance to pathogen attack.

A transgene, such as a nucleotide sequence selected in accordance with the present invention, is expressed in a transformed plant to produce in the cell a protein encoded thereby. Briefly, transcription of the DNA sequence is initiated by the binding of RNA polymerase to the DNA sequence's promoter region. During transcription, movement of the RNA polymerase along the DNA sequence forms messenger RNA ("mRNA") and, as a result, the DNA sequence is transcribed into a corresponding mRNA. This mRNA then moves to the ribosomes of the rough endoplasmic reticulum which, with transfer RNA ("tRNA"), translates the mRNA into the protein encoded thereby. Proteins of the present invention thus produced in a transformed host then perform an important function in the plant's signal transduction pathway corresponding to pathogen resistance. Although the sequence of events involved in the resistance mechanism is not well understood, it is clear that proteins contemplated by the present invention enhance a plant's resistance response by participating in this signal transduction pathway.

To comment generally upon plant resistance to pathogens, plants respond to pathogen infection in various ways, including a rapid induction of localized necrosis at the site of infection (the hypersensitive response, HR), production of antimicrobial compounds, lignin formation, oxidative burst, and increased expression of defense-related genes. Two categories of genes and, therefore, proteins are involved in a plant's response system, disease resistance (R) genes and defense genes. R genes typically encode proteins which play a role in pathogen recognition and/or signal transduction.

R genes may be identified based upon their polymorphism in a particular plant species. That is, some crop varieties contain a particular R gene and others will lack that gene. Analysis of the progeny of genetic crosses between resistant and susceptible crop varieties allow the mapping of R genes to specific regions on a chromosome. R genes frequently, although not always, display dominant gene action and play a major qualitative role in conferring disease resistance. They frequently map to single loci in the genome and are often found to be members of a gene family. R genes differ from other genes that may play a role in disease resistance later in the defense response (after pathogen recognition). These other "downstream" genes are often referred to as "defense genes" or "defense-related genes" and include the class of genes known as "pathogenesis-related" (PR) genes.

With regard to increased expression of defense-related genes, it has long been recognized that transcriptional activation of a battery of plant defense-related genes is commonly associated with pathogen invasion. Defense genes include, for example, those encoding pathogenesis related proteins (PRs), hydroxyproline rich glycoproteins, and enzymes for phytoalexin biosynthesis such as phenylalanine ammonia lyase (PAL) and chalcone sythase. Although the role of these proteins in plant disease resistance is not well understood, their enzymatic functions indicate that they are well suited for defense against pathogens. Results of preliminary research have spurred extensive investigations into the biological function of defense genes and mechanisms by which they are activated.

With respect to R genes, it has been postulated that disease resistance of a plant may be induced by the genetic interaction of single genes in both the pathogen and the plant host. The phenomenon of disease resistance is believed to be initiated by physical contact between a pathogen and a potentially compatible portion of the host. Once such contact has occurred, usually as a result of wind or rain vectored deposition of the pathogen, the pathogen must recognize that such contact has been established in order to initiate the pathogenic process. Likewise, such recognition by the host is required in order to initiate a resistance response. A great deal of research is currently focused upon elucidating the precise manner in which such recognition occurs. Pathogen recognition is believed to be associated with low pH of plant tissues or the presence of plant-specific metabolites. It is believed that plant recognition occurs as a result of a race-specific mechanism where the protein product of a host disease resistance (R) gene recognizes the product of an avirulence gene of the pathogen. As a result, the plant's defense responses are activated, leading to production of various factors (e.g., gum or cork production, production of inhibitors of pathogen proteases, deposition of lignin and hydroxyproplin-rich proteins in cell walls) and offensive resistance factors (e.g., production of phytoalexins, secreted chitinases). If the rate and level of activation of the genes producing these factors is sufficiently high, the host is able to gain an advantage on the pathogen. On the other hand, if the pathogen is fully activated at an earlier stage in the infection process, it may overwhelm both the offensive and defensive resistance factors of the plant.

In this regard, much effort has been focused on the characterization of cis-acting elements involved in elicitor- and pathogen-induced defense gene expression, and a few putative transcription factors involved in defense responses have been identified. Many defense-related genes are induced in both compatible (susceptible) and incompatible (resistant) plant-pathogen interactions. However, the expression of many defense genes is more rapid and pronounced in a plant challenged with an incompatible pathogen. In many plant-pathogen interactions, these defense responses are activated upon recognition of a pathogen carrying a specific avirulence (avr) gene by a plant host containing a corresponding R gene. In particular, incompatible interactions involving a plant R gene and a corresponding pathogen avr gene lead to accelerated plant defense gene expression. Many R genes encode proteins that are likely involved either in the recognition of signals determined by avr genes or in the early steps of signal transduction. However, a direct link between any R gene and defense gene activation has not previously been established.

In tomato, resistance to the bacterial pathogen *Pseudomonas syringae* pv. tomato (which causes bacterial speck disease) has been shown to be associated with a single locus (Pto) that displays dominant gene action. Resistance of plants carrying the Pto locus to *Pseudomonas syringae* pv. tomato strains expressing the avirulence gene avrPto is a model system for signal transduction pathways mediated by a specific R gene. This system constitutes the only example of R gene mediated resistance pathway in which genes for multiple components have been cloned. Currently, three components are known to be involved in the signaling pathway mediated by Pto: the serine/threonine protein kinase Pto, a second serine/threonine kinase Pti1, and the leucine-rich-repeat type protein Prf. The Pto gene was originally discovered in *Lycopersicon pimpinellifolium*, a wild tomato species, and isolated by map-based cloning. Mutagenesis of a bacterial speck-resistant tomato line revealed a second gene, Prf, that is required for both Pto-mediated resistance and fenthion sensitivity, a related phenotype mediated by the Fen gene. Using the yeast two-hybrid system with Pto as a bait, the present inventors have identified another protein kinase Pti1 that appears to act downstream of Pto and is involved in the hypersensitive response.

In accordance with the present invention, three additional Pto-interacting proteins, Pti4, Pti5 and Pti6, also referred to herein as Pti4/5/6, that belong to a large family of plant transcription factors, are characterized. These proteins bind to a cis-element that is widely conserved among "pathogenesis-related" (PR) genes and are implicated in the regulation of these genes during incompatible plant-pathogen interactions. Pti4/5/6 each have characteristics that are typical of transcription factors. The present inventors have discovered that Pti4/5/6 specifically recognize and bind to a DNA sequence that is present in the promoter region of a large number of genes encoding PR proteins. Therefore, a direct connection has been discovered between a disease resistance gene and the specific activation of plant defense genes.

SUMMARY OF THE INVENTION

The present invention relates to the isolation, purification and use of nucleotide sequences, such as, for example, Pti4, Pti5 and Pti6 ("Pti4/5/6"), which are useful for enhancing a plant's ability to resist pathogen-related disease by encoding transcription factors that enhance a plant's ability to activate defense mechanisms when faced with pathogen activity. Proteins encoded by Pti4/5/6 are useful for enhancing a plant's ability to resist pathogen attack. The proteins encoded by the Pti4/5/6 nucleotide sequences each possess a DNA binding domain, putative nuclear localization sequences (NLS) and regions rich in acidic amino acids.

It is presently shown that the newly-isolated DNA sequences of Pti4/5/6 encode transcription factors which physically interact with Pto kinase. The present invention provides a novel form of plant protection against many types of pathogens including viruses, bacteria and fungi. While it is not intended that the present invention be limited by any mechanism whereby it achieves its advantageous result, it is believed that manipulation of these transcription factors enables the coordinate regulation of large numbers of genes involved in plant disease resistance. The invention therefore, features the DNA sequences of the Pti4/5/6 genes and the amino acid sequences of the Pti4/5/6 proteins, as set forth herein, as well as DNA sequences and amino acid sequences having substantial identity thereto and having similar levels of activity. Inventive genes may be inserted into an expression vector to produce a recombinant DNA expression system which is also an aspect of the invention.

In one aspect of the invention, inventive DNA sequences conferring disease resistance to plants are used to transform cells and to transform plants. In another aspect of the invention, there is provided a process of conferring disease resistance to plants by growing plant cells transformed with an inventive recombinant DNA expression vector and capable of expressing the DNA sequences. Plants transformed with inventive nucleotide sequences thereby have an enhanced ability to resist attack by pathogens which have an avr gene corresponding to a plant resistance gene.

It is an object of the present invention to provide isolated, sequenced and purified proteins which are useful for conferring disease resistance to a plant.

Another object of the invention is to provide isolated nucleotide sequences which encode said proteins and thereby find advantageous use when incorporated into a vector or plasmid as a transformant for a plant or microorganism.

Additionally, it is an object of the invention to provide transformed plants which have enhanced ability to resist attack by pathogens.

Further objects, advantages and features of the present invention will be apparent from the detailed description herein.

BRIEF DESCRIPTION OF THE FIGURES

Although the characteristic features of this invention will be particularly pointed out in the claims, the invention itself, and the manner in which it may be made and used, may be better understood by referring to the following description taken in connection with the accompanying figures forming a part hereof.

FIG. 1 sets forth a comparative alignment of Pti4/5/6 amino acid sequences (SEQ ID NO:1, SEQ ID NO:2 and SEQ ID NO:3, respectively). The Pretty Box program (GCG package, version 7.0) was used to create the best alignment. Also set forth in FIG. 1 are amino acid consensus 1 motif ("A") and amino acid consensus 2 motif ("B").

DETAILED DESCRIPTION OF THE INVENTION

Figure 2:
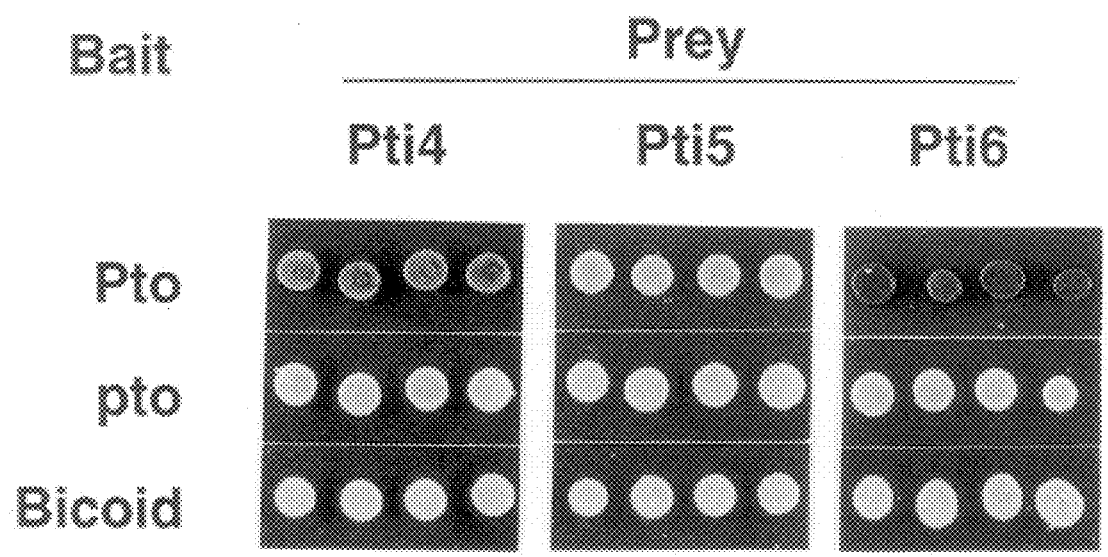
FIG. 2 sets forth results of the Experiment described in Example 1 herein. Briefly, EGY48 yeast cells containing a prey of Pti4, Pti5 or Pti6 (in pJG4–5), and a bait of Pto, pto or Bicoid (in pEG202) were grown on galactose Ura⁻His⁻Trp⁻X-Gal medium. The plates were incubated at 30° C. for three days and photographed. Four independent, representative colonies are shown for each bait/prey combination.

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention as described herein being contemplated as would normally occur to one skilled in the art to which the invention pertains.

The present invention relates to nucleotide sequences which confer disease resistance to plants by encoding proteins that physically interact with proteins encoded by R genes to enhance the activation of plant defense genes such as, for example, PR genes. The present inventors have isolated, sequenced and characterized three biologically and commercially useful proteins (Pto-interacting proteins, or "Pti" proteins), Pti4/5/6, and have isolated, sequenced and cloned three novel nucleotide sequences which encode them, Pti4/5/6. When heightened expression of inventive nucleotide sequences is achieved in a plant in accordance with the present invention, the plant will have the improved ability to resist pathogen attack. As such, advantageous features of the present invention include the transformation of a wide variety of plants of various agriculturally and/or commercially valuable plant species to provide advantageous resistance to pathogen attack. Three amino acid sequences according to the invention are set forth in SEQ ID NO:1 (Pti4), SEQ ID NO:2 (Pti5) and SEQ ID NO:3 (Pti6). The terms "protein" and "amino acid sequence" are used interchangeably herein to designate a plurality of amino acids linked in a serial array. Skilled artisans will recognize that through the process of mutation and/or evolution, proteins of different lengths and having differing constituents, e.g., with amino acid insertions, substitutions, deletions, and the like, may arise that are related to the proteins of the present invention by virtue of (a) amino acid sequence homology; and (b) good functionality with respect to pathogen resistance. Many deletions, insertions, and, especially, substitutions, are not expected to produce radical changes in the characteristics of the protein. However, when it is difficult to predict the exact effect of the substitution, deletion, or insertion in advance of doing so, one skilled in the art will appreciate that the effect may be evaluated by routine screening assays.

In addition to the above explicitly named proteins, therefore, the present invention also contemplates proteins having substantial identity to those set forth herein. The term "substantial identity," as used herein with respect to an amino acid sequence, is intended to mean sufficiently similar to cause improved pathogen resistance when expressed in a plant transformed in accordance with the invention. In one preferred aspect of the present invention, variants having such potential modifications as those mentioned above, which have at least about 50% identity to the amino acid sequences set forth in SEQ ID NOS: 1, 2 and 3, are considered to have "substantial identity" thereto. Sequences having lesser degrees of identity but comparable biological activity are considered to be equivalents. It is believed that the identity required to maintain proper functionality is related to maintenance of the tertiary structure of the protein such that specific interactive sequences will be properly located and will have the desired activity. As such, it is believed that there are discreet domains and motifs within the amino acid sequence which must be present for the protein to retain it advantageous functionality and specificity. While it is not intended that the present invention be limited by any theory by which it achieves its advantageous result, it is contemplated that a protein including these discreet domains and motifs in proper spatial context will retain good activity with respect to interaction with R gene products, even where substantial substitutions, insertions and/or deletions have taken place elsewhere in the sequence.

In this regard, a protein will find advantageous use according to the invention if it includes one or more amino acid consensus motifs and possesses substantially similar activity with respect to a protein set forth in SEQ ID NO:1, 2 or 3. The term "amino acid consensus motif" as used herein is intended to designate all or a portion of an inventive amino acid sequence which is substantially conserved among inventive proteins. For example, referring to FIG. 1, the box labeled "A" includes amino acid consensus 1 motif and includes generally the following sequence:

--SEQ ID NO:7 --X-- SEQ ID NO:8 --X-- SEQ ID NO:9 --X-- SEQ ID NO:10 --X-- SEQ ID NO:11 wherein "--X--" indicates that one or more amino acids may be present at that location, but not exceeding about 15 amino acids. Thus, consensus 1 motif is also represented by the following:

His/Lys Tyr/Phe Arg Gly Val Arg Gln/Arg Arg Pro Trp Gly Lys/Arg Phe/Tyr/Trp Ala Ala Glu Ile Arg Asp Pro/Ser Ala/Thr Lys/Arg --X-- Gly Ala/Lys Arg Val Trp Leu Gly Thr Tyr/Phe Glu/Asp Thr Ala/Pro Glu Glu Ala Ala --X-- Ala/Val Tyr Asp Lys/Arg Ala Ala --X-- Arg/Lys Met/Leu Arg/Lys Gly Ser/Ala/Pro Lys/Asp Ala --X-- Leu/Thr Asn Phe Pro wherein a "/" between two or in a series of amino acids indicates that any one of the amino acids indicated may be present at that location; and wherein "--X--" indicates that one or more amino acids may be present at that location, but not exceeding about 15 amino acids. The box labeled "B" includes amino acid consensus 2 motif and includes generally the following sequence:

--SEQ ID NO:12 --X-- SEQ ID NO:13 --X-- SEQ ID NO:14 --X-- Leu --X-- Asp/Glu --X-- Ala Leu wherein a "/" between two or in a series of amino acids indicates that any one of the amino acids indicated may be present at that location, and wherein "--X--" indicates that one or more amino acids may be present at that location, but not exceeding about 15 amino acids. Thus, consensus 2 motif is also represented by the following:

Asp Leu Pro Leu --X-- Asp/Asn Ser Glu/Gln --X-- Met Val Ile/Leu/Val Tyr --X-- Leu --X-- Asp/Glu --X-- Ala Leu wherein a "/" between two or in a series of amino acids indicates that any one of the amino acids indicated may be present at that location; and wherein "--X--" indicates that one or more amino acids may be present at that location, but not exceeding about 15 amino acids. A protein comprising amino acid consensus 1 motif and/or amino acid consensus 2 motif and having substantially similar functionality to amino acid sequences set forth herein are intended to fall within the scope of the invention.

In a preferred aspect of the invention, nucleotide sequences encoding inventive proteins have the nucleotide sequences set forth herein as SEQ ID NO:4 (Pti4), SEQ ID NO:5 (Pti5) and SEQ ID NO:6 (Pti6).

The term "nucleotide sequence" is intended to refer to a natural or synthetic linear and sequential array of nucleotides and/or nucleosides, and derivatives thereof. Nucleotide sequences selected for use in accordance with the invention may be cloned from cDNA libraries corresponding to a wide variety of plant species. The present invention also contemplates nucleotide sequences having substantial identity to those set forth in SEQ ID NOS. 1, 2 and 3. The term "substantial identity" is used herein with respect to a nucleotide sequence to designate that the nucleotide sequence has a sequence sufficiently similar to one of those explicitly set forth above that it will hybridize therewith under moderately stringent conditions, this method of determining identity being well known in the art to which the invention pertains. Briefly, moderately stringent conditions are defined in Sambrook et al., *Molecular Cloning: a Laboratory Manual*, 2ed. Vol. 1, pp. 101–104, Cold Spring Harbor Laboratory Press (1989) as including the use of a prewashing solution of 5× SSC, 0.5% SDS, 1.0 mM EDTA (pH 8.0) and hybridization and washing conditions of about 55° C., 5× SSC. A further requirement of the term "substantial identity" as it relates to an inventive nucleotide sequence is that it must encode an inventive protein, i.e. one which is capable of physically interacting with an R gene product in a manner which enhances a plant's ability to resist pathogens.

Suitable DNA sequences according to the invention may be obtained, for example, by cloning techniques, these techniques being well known in the relevant art, or may be made by chemical synthesis techniques which are also well known in the art. Suitable nucleotide sequences may be isolated from DNA libraries obtained from a wide variety of species by means of nucleic acid hybridization or PCR, using as hybridization probes or primers nucleotide sequences selected in accordance with the invention, such as those set forth in SEQ ID NOS: 4, 5 and 6; nucleotide sequences having substantial identity thereto; or portions thereof. In certain preferred aspects of the invention, nucleotide sequences from a wide variety of plant species may be isolated and/or amplified which encode Pti4/5/6, or proteins having substantial identity thereto and having excellent activity with respect to interaction with R gene products native to that species or R gene products of other plant species. It is expected that nucleotide sequences specifically set forth herein or selected in accordance with the invention may be advantageously used in a wide variety of plant species, including but not limited to a species from which it is isolated.

In certain preferred aspects of the invention, a PCR primer is selected for use as described above based upon the presence therein of a nucleotide consensus motif. The term "nucleotide consensus motif" as used herein is intended to designate all or a portion of an inventive nucleotide sequence, which encodes an amino acid sequence having substantial identity to an amino acid consensus motif (described herein). For example, a suitable nucleotide consensus motif, designated "nucleotide consensus 1 motif," is one which encodes an amino acid sequence within the scope of amino acid consensus 1 motif. Another is "nucleotide consensus 2 motif," which is a nucleotide sequence which encodes an amino acid sequence within the scope of amino acid consensus 2 motif.

It is readily understood that other nucleotide sequences may be advantageously selected for use in PCR primers designed to identify/isolate/amplify analogs to Pti4/5/6 in a wide variety of plant species. For instance, variations in a nucleotide consensus motif which are silent (i.e., do not result in the substitution of a different amino acid in the encoded protein), may advantageously be included in a nucleotide sequence used as a PCR primer in accordance with the invention.

DNA sequences selected for use in accordance with the invention can be incorporated into the genomes of plant or bacterium cells using conventional recombinant DNA technology, thereby making transformed plants having an enhanced ability to resist pathogen attack. In this regard, the term "genome" as used herein is intended to refer to DNA which is present in the plant or microorganism and which is heritable by progeny during propagation of the plant or microorganism. As such, inventive transgenic plants may alternatively be produced by breeding a transgenic plant made according to the invention with a second plant or selfing an inventive transgenic plant to form an F1 or higher generation plant. Transformed plants and progeny thereof are all contemplated by the invention and are all intended to fall within the meaning of the term "transgenic plant."

Generally, transformation of a plant involves inserting a DNA sequence into an expression vector in proper orientation and correct reading frame. The vector contains the necessary elements for the transcription of the inserted protein-encoding sequences. A large number of vector systems known in the art can be advantageously used in accordance with the invention, such as plasmids, bacteriophage viruses or other modified viruses. Suitable vectors include, but are not limited to the following viral vectors: lambda vector system λgt11, λgt10, Charon 4, and plasmid vectors such as pBI121, pBR322, pACYC177, pACYC184, pAR series, pKK223-3, pUC8, pUC9, pUC18, pUC19, pLG339, pRK290, pKC37, pKC101, pCDNAII, and other similar systems. The DNA sequences are closed into the vector using standard cloning procedures in the art, as described by Maniatis et al., *Molecular Cloning: A Laboratory Manual,* Cold Springs Laboratory, Cold Springs Harbor, N.Y. (1982), which is hereby incorporated by reference. The plasmid pBI121 is available from Clontech Laboratories, Palo Alto, Calif. It is understood that related techniques may be advantageously used according to the invention to transform microorganisms such as, for example, Agrobacterium, yeast, *E. coli* and Pseudomonas.

In order to obtain efficient expression of the gene or gene fragment of the present invention, a promoter must be present in the expression vector. An expression vector according to the invention may be either naturally or artificially produced from parts derived from heterologous sources, which parts may be naturally occurring or chemically synthesized, and wherein the parts have been joined by ligation or other means known in the art. The introduced coding sequence is under control of the promoter and thus will be generally downstream from the promoter. Stated alternatively, the promoter sequence will be generally upstream (i.e., at the 5' end) of the coding sequence. As such, in one representative example, enhanced Pti4/5/6 production may be achieved by inserting a Pti4/5/6 nucleotide sequence in a vector downstream from and operably linked to a promoter sequence capable of driving constitutive high-level expression in a host cell. Two DNA sequences (such as a promoter region sequence and a Pti-encoding sequence) are said to be operably linked if the nature of the linkage between the two DNA sequences does not (1) result in the introduction of a frame-shift mutation, (2) interfere with the ability of the promoter region sequence to direct the transcription of the desired Pti-encoding gene sequence, or (3) interfere with the ability of the desired Pti sequence to be transcribed by the promoter region sequence.

RNA polymerase normally binds to the promoter and initiates transcription of a DNA sequence or a group of linked DNA sequences and regulatory elements (operon). Promoters vary in their strength, i.e. their ability to promote transcription. Depending upon the host cell system utilized, a wide variety of suitable promoters can be used, and many are well known in the art. For example, a gene product may be obtained using a constitutive (e.g. Cauliflower Mosaic Virus 35S promoter), inducible (e.g. tomato E8 ethylene inducible promoter), developmentally regulated (e.g. Tomato polygalacturonase promoter) or tissue specific promoter to construct the vectors. Alternative promoters which may be suitably used in accordance with the invention include Figwort mosaic virus (FMV) promoter, Octopine synthase (OCS) promoter and also the native Pti4/5/6 promoter. It is not intended, however, that this list be limiting, but only provide examples of promoters which may be advantageously used in accordance with the present invention.

As briefly mentioned above, it is well known that there may or may not be other regulatory elements (e.g., enhancer sequences) which cooperate with the promoter and a transcriptional start site to achieve transcription of the introduced (i.e., foreign) sequence. The phrase "under control of" contemplates the presence of such other elements as are necessary to achieve transcription of the introduced sequence. Also, the recombinant DNA will preferably include a termination sequence downstream from the introduced sequence.

Once the defense gene of the present invention has been cloned into an expression system, it is ready to be transformed into a host cell, such as, for example, a plant cell. Plant tissue suitable for transformation in accordance with certain preferred aspects of the invention include whole plants, leaf tissues, flower buds, root tissues, meristems, protoplasts, hypocotyls and cotyledons. It is also understood, however, that this list is not intended to be limiting, but only provide examples of tissues which may be advantageously transformed in accordance with the present invention.

One technique of transforming plants with the gene conferring disease resistance in accordance with the present invention is by contacting the tissue of such plants with an inoculum of a bacteria transformed with a vector comprising a DNA sequence selected in accordance with the present invention. Generally, this procedure involves inoculating the plant tissue with a suspension of bacteria and incubating the tissue for about 48 to about 72 hours on regeneration medium without antibiotics at about 25–28° C.

Bacteria from the genus Agrobacterium may be advantageously utilized to transform plant cells. Suitable species of such bacterium include *Agrobacterium tumefaciens* and *Agrobacterium rhizogenes*. *Agrobacterium tumefaciens* (e.g., strains LBA4404 or EHA105) is particularly useful due to its well-known ability to transform plants. Another technique which may advantageously be used is vacuum-infiltration of flower buds using Agrobacterium-based vectors.

Another approach to transforming plant cells with a DNA sequence selected in accordance with the present invention involves propelling inert or biologically active particles at plant tissues or cells. This technique is disclosed in U.S. Pat. Nos. 4,945,050, 5,036,006 and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector. Alternatively, the target cell can be surrounded by the vector so that the vector is carried into the cell by the wake of the particle. Biologically active particles (e.g., dried yeast cells, dried bacterium or a bacteriophage, each containing DNA material sought to be introduced) can also be propelled into plant cells. It is not intended, however, that the present invention be limited by the choice of vector or host cell. It should of course be understood that not all vectors and expression control sequences will function equally well to express the DNA sequences of this invention. Neither will all hosts function equally well with the same expression system. However, one of skill in the art may make a selection among vectors, expression control sequences, and hosts without undue experimentation and without departing from the scope of this invention.

Once the recombinant DNA is introduced into the plant tissue, successful transformants can be screened using standard techniques such as the use of marker genes, e.g., genes encoding resistance to antibiotics. Additionally, the level of expression of the foreign DNA may be measured at the transcriptional level or as protein synthesized.

An isolated DNA sequence selected in accordance with the present invention may be utilized in an expression system to improve disease resistance in a wide variety of plant cells, including gymnosperms, monocots and dicots. These DNA sequences are particularly useful in crop plant cells such as rice, wheat, barley, rye, corn, potato, carrot, sweet potato, bean, pea, chicory, lettuce, cabbage, cauliflower, broccoli, turnip, radish, spinach, asparagus, onion, garlic, eggplant, pepper, celery, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane. According to one preferred aspect of the invention, the target plant is a tomato plant or a potato plant. According to another preferred aspect of the invention, the target plant is a monocot such as, for example, rice, wheat or corn. The present invention may also be used in conjunction with non-crop plants, such as, for example, *Arabidopsis thaliana*.

Those skilled in the art will recognize the agricultural advantages inherent in plants constructed to have increased or selectively increased expression of Pti4/5/6 and/or of nucleotide sequences which encode proteins having substantial identity thereto. Such plants are expected to have substantially improved resistance to pathogens and, therefore, will also be expected to have improved yield as compared to a corresponding non-transformed plant. Additionally, the present invention not only provides plants capable of minimizing immediate damage caused by pathogens, but is also useful to prevent the establishment of a strong pathogen population in a given area such as, for example, a given corn field.

The invention will be further described with reference to the following specific Examples. It will be understood that these Examples are illustrative and not restrictive in nature.

EXAMPLE ONE

Yeast Two-Hybrid Interaction of Pto with Pti4/5/6

Yeast strains carrying the Pto bait and a prey of Pti4, Pti5 or Pti6 grew in the absence of leucine, indicative of the LEU2 reporter gene activation. When grown on X-Gal plates, these yeast cells were blue as a result of the lacZ reporter gene activation. As determined by the intensity of blue color, the strength of interaction of Pto with these three preys is in the order of Pti6>Pti4>Pti5. In contrast, control yeast strains expressing the arbitrary bait Bicoid and any one of the three preys did not activate the LEU2 or the LacZ reporter genes. FIG. 2 shows the specific interaction of Pti4, Pti5 and Pti6 with Pto in yeast. This test indicates that the interactions of these Pti proteins with Pto were specific.

EXAMPLE TWO

DNA Blot Analysis of Tomato Genomic DNA

Figure 3:
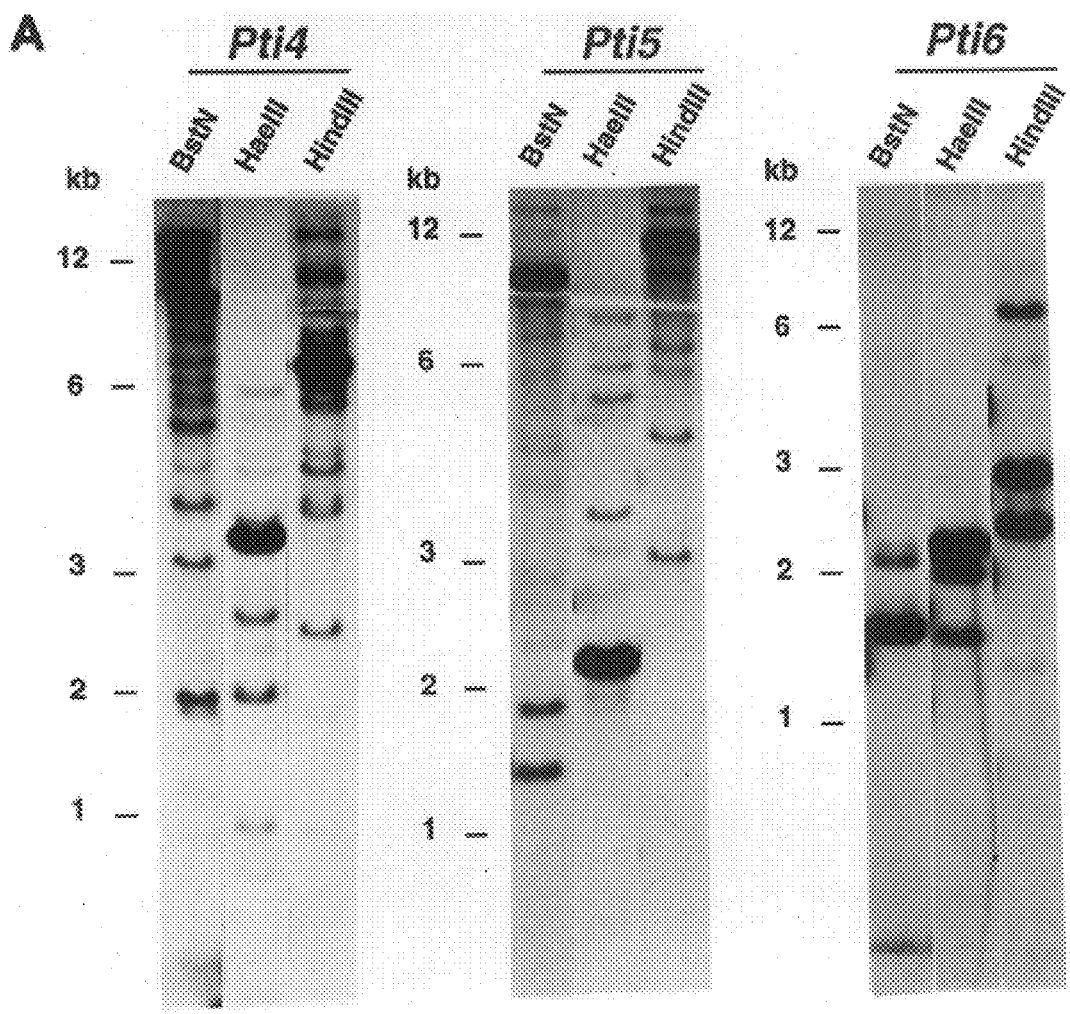
FIG. 3 sets forth the results of the gel blot analysis procedure described in Example 2 herein.

Genomic DNA (5 μg/lane) from Rio Grande-PtoR plants was digested with the indicated restriction enzymes, and the DNA blot was hybridized to the Pti456 cDNA probes. Results are set forth in FIG. 3 herein and deduced sequences are set forth herein as SEQ ID NOS: 4, 5 and 6

EXAMPLE THREE

Cloning of Pti4/5/6 Inserts into Fusion Protein Expression Vectors in E. coli The Pti1 cDNA was removed from the GST-Pti1 fusion plasmid (Zhou, J., Loh, Y.-T., Bressan, R. A. and Martin, G. (1995). The tomato gene Pti1 encodes a serine/threonine kinase that is phosphorylated by Pto and is involved in the hypersensitive response. Cell 83, 925–935.) with EcoRI and XhoI and replaced with cDNA inserts of Pti4/5/6 to create GST-Pti4/5/6 fusion constructs. Pti4 cDNAs (nucleotides 13–993) and Pti5 cDNA (nucleotides 82–782) were excised form pJG4-5 with EcoRI and XhoI before ligation into the pGEX vector. The full length Pti6 insert was PCR-amplified using the full length Pti6 cDNA clone in pBluescript SK(-) (Stratagene) as a template and the upstream primer 5'-GAGAATTCATGACGGAAA ATTCAG-3' (SEQ ID NO:15) and the T7 primer 5'- AATACGACTCACTATAG-3' (SEQ ID NO:16). The PCR product was first digested partially with EcoRI and then digested completely with XhoI before being inserted into the GST-expression vector. The resulting constructs were introduced into E. coli strain PR745 (Ion-New England Biolabs, Beverly, Mass.), and GST-fusion proteins were expressed and purified as described by Guan, K.-L., and Dixon, J. E. (1991). Eukaryotic proteins expressed in Escherichia coli: an improved thrombin cleavage and purification of fusion proteins with glutathione S-transferase. Anal. Biochem. 192, 262–267.

EXAMPLE FOUR

Gel-Mobility Shift Assay

Figure 4:
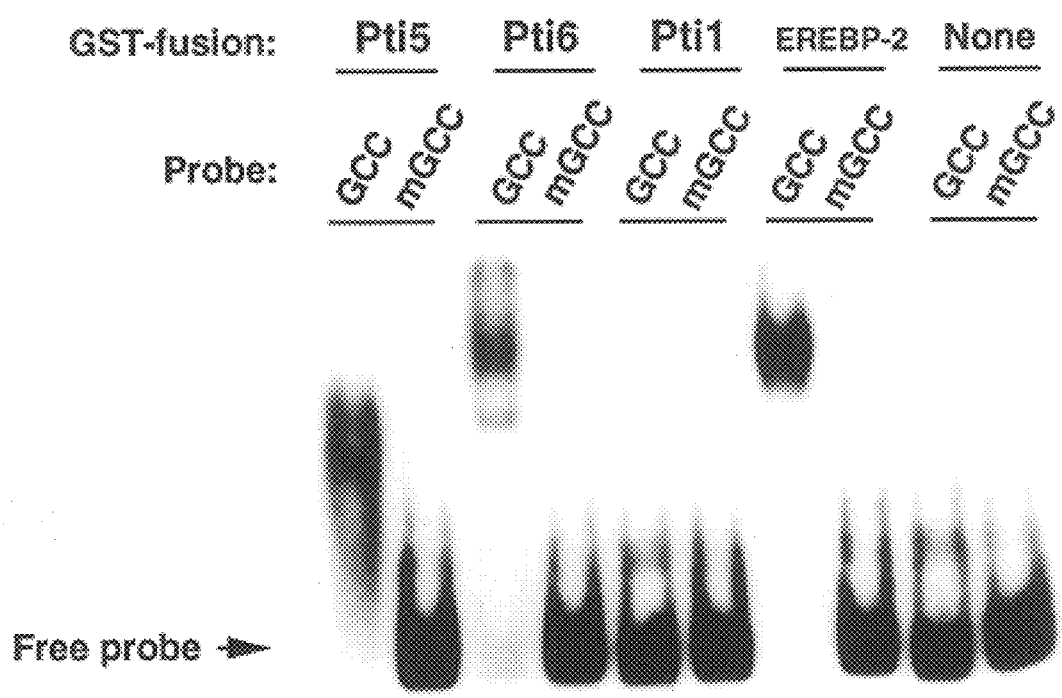
FIG. 4 sets forth the results of the gel mobility-shift assay described in Example 4 herein.

The wild type gln2 PR-box 2× (CATAAGAGCCGCCACTAAAATAA GACCGATCAAATAAGAGCCGCCAT)(SEQ ID NO:17) and mutated PR-box 2× (CATAAGATCCTCCACTAAAATAAGACCGATCAAA AAGATCCTCCAT) (SEQ ID NO:18) were end-labeled by 32P as described by Ausubel, F. M., Brent, R., Kingston, R. E., Moore, D. D., Seidman, J. G., Smith, J. A., and Struhl, K. (1994). Current Protocols in Molecular Biology. (New York: Greene Publish Associates/John Wiley and Sons). Four fmol of probe was mixed with each of the purified GST-fusion proteins in a buffer containing 2 μg poly(dA-dT) (dA-dT), 25 mM Hepes (PH7.5), 40 mM KCl, 0.1 mM EDTA, 10% glycerol, and 1 mM DTT, incubated at room temperature for 15 minutes, and electrophoresed on a 4% polyacrylamide gel in 0.25×TBE buffer. Ohme-Takagi, M. and Shinshi, H. (1995). Ethylene-inducible DNA-binding proteins that interact with an ethylene-responsive element. Plant Cell 7, 173–182. The gel was subsequently dried and exposed to x-ray film. As shown in FIG. 4, both GST-Pti5 and GST-Pti6 bound the wild type PR-box. No binding was detected when the mutated PR-box was used in the assay, indicating that binding of GST-Pti5 and GST-Pti6 to the PR-box was highly specific. In contrast to GST-Pti5 and GST-Pti6, neither GST-Pti1 nor GST itself bound to the PR-box. These results further confirmed the specificity of binding of Pti5 and Pti6 to the gln2 PR-box.

EXAMPLE FIVE

Plant Inoculation and RNA Blot Analysis

Leaves of 7-week old tobacco plants were injected with P.s. tabaci strain 11528R race 0 or the same strain carrying the avrPto gene in pPTE6 (Ronald, P. C., Salmeron, J. M., Carland, F. M., and Staskawicz, B. J. (1992). The cloned avirulence gene avrPto induces disease resistance in tomato cultivars containing the Pto resistance gene. J. Bacteriol. 174, 1604–1611.) at $10^6$ cfu/ml or $10^8$ cfu/ml, harvested at various time points following inoculation, and total RNA was extracted. Ten μg RNA per sample was separated on 1% formaldehyde agarose gel, and duplicate RNA blots were hybridized to the following probes as described by Zhou, J., Loh, Y.-T., Bressan, R. A. and Martin, G. (1995). The tomato gene Pti1 encodes a serine/threonine kinase that is phosphorylated by Pto and is involved in the hypersensitive response. Cell 83, 925–935.: PRP1, CHN50, and Osmotin.

What is claimed is:

1. A plant transformed with a foreign nucleotide sequence encoding a protein that has pathogen resistance activity in the plant, wherein the protein has at least about 50% identity to the protein of SEQ ID NO:1, SEQ ID NO:2 or SEQ ID NO:3.

2. The plant in accordance with claim 1 wherein the nucleotide sequence comprises a sequence selected from the group consisting of:
   (i) bases 35 to 736 of SEQ ID NO:4,
   (ii) bases 2 to 484 of SEQ ID NO:5, and
   (iii) bases 312 to 1055 of SEQ ID NO:6.

3. The plant in accordance with claim 1 wherein said plant is transformed with a vector that comprises the foreign nucleotide sequence.

4. The plant in accordance with claim 3 wherein the vector further comprises regulatory elements flanking and operably linked to the nucleotide sequence, the regulatory elements controlling expression of the sequences in the plant.

5. The plant according to claim 1, the plant being selected from the group consisting of a monocot and a dicot.

6. The plant according to claim 1 wherein the protein comprises a motif having the amino acid sequence of:
   SEQ ID NO:7 --X-- SEQ ID NO:8 --X-- SEQ ID NO:9 --X-- SEQ ID NO:10 --X-- SEQ ID NO:11,
wherein "--X--" represents from zero to about 15 naturally occurring amino acids.

7. The plant in accordance with claim 1 wherein the protein comprises an amino acid sequence selected from the group consisting of:
   (I) the amino acid sequence of SEQ ID NO:1,
   (ii) the amino acid sequence of SEQ ID NO:2, and
   (iii) the amino acid sequence of SEQ ID NO:3.

8. A progeny plant of the plant of claim 3, wherein the progeny plant comprises the foreign nucleotide sequence.

9. A method for producing a transformed plant having an enhanced ability to resist pathogens compared to a non-transformed plant, comprising:
   providing a vector comprising a nucleotide sequence encoding a protein, and regulatory elements flanking and operably linked to the nucleotide sequence, the regulatory elements controlling expression of the protein in the plant; and
   transforming a target plant with the vector to provide a transformed plant, wherein the transformed plant expresses the protein, and wherein the protein has at least about 50% identity to the protein of SEQ ID NO:1, SEQ ID NO:2 or SEQ ID NO:3 and has pathogen resistance activity.

10. The method according to claim 9, wherein the target plant is selected from the group consisting of a monocot and a dicot.

11. The method according to claim 9, wherein the protein comprises a motif having the amino acid sequence of:
    SEQ ID NO:7 --X-- SEQ ID NO:8 --X-- SEQ ID NO:9 --X-- SEQ ID NO:10 --X-- SEQ ID NO:11,
wherein "--X--" represents from zero to about 15 naturally occurring amino acids.

12. The method according to claim 9, wherein the regulatory elements comprise a plant promoter.

13. The method in accordance with claim 9 wherein the protein comprises an amino acid sequence selected from the group consisting of:
    (I) the amino acid sequence of SEQ ID NO:1,
    (ii) the amino acid sequence of SEQ ID NO:2, and
    (iii) the amino acid sequence of SEQ ID NO:3.

14. The method in accordance with claim 9 wherein the nucleotide sequence comprises a sequence selected from the group consisting of:

(i) bases 35 to 736 of SEQ. ID NO:4, (ii) bases 2 to 484 of SEQ ID NO:5, and (iii) bases 312 to 1055 of SEQ ID NO:6.

15. A transformed plant obtained according to the method of claim 9.

16. A progeny plant of the plant of claim 15, wherein the progeny plant comprises the nucleotide sequence.

17. A method for transforming a target plant cell, comprising:

providing a vector comprising a nucleotide sequence encoding a protein, and regulatory elements flanking and operably linked to the nucleotide sequence, the regulatory elements controlling expression of the protein in a plant; and transforming the target plant cell with the vector to provide a transformed plant cell, wherein the transformed plant cell expresses the protein; and wherein the protein has at least about 50% identity to the protein of SEQ ID NO:1, SEQ ID NO:2 or SEQ ID NO:3 and has pathogen resistance activity.

18. The method according to claim 17, wherein the nucleotide sequence comprises the nucleotide sequence of SEQ ID NO:4, SEQ ID NO:5 or SEQ ID NO:6.

19. A transformed plant cell prepared according to the method of claim 17.

20. A method of producing a transformed plant, comprising incorporating into the nuclear genome of the plant an isolated nucleotide sequence which encodes a protein to provide a transformed plant that expresses the protein in an amount effective to enhance the ability of the transformed plant to resist pathogens compared to a nontransformed plant;

wherein the protein has at least about 50% identity to the protein of SEQ ID NO:1, SEQ ID NO:2 or SEQ ID NO:3 and has pathogen resistance activity.

21. The method according to claim 20, wherein the protein comprises the amino acid sequence of SEQ ID NO:1, SEQ ID NO:2 or SEQ ID NO:3.

22. The method in accordance with claim 20 wherein the protein comprises a motif having the amino acid sequence of:

SEQ ID NO:7 --X-- SEQ ID NO:8 --X-- SEQ ID NO:9 --X-- SEQ ID NO:10 --X-- SEQ ID NO:11, wherein "--X--" represents from zero to about 15 naturally occurring amino acids.

23. The method of claim 20, wherein the protein has at least about 50% identity to the amino acid sequence of SEQ ID NO:1.

24. The method of claim 20, wherein the nucleotide sequence comprises bases 35 to 736 of SEQ ID NO:4.

25. The method of claim 20, wherein the protein has at least about 50% identity to the amino acid sequence of SEQ ID NO:2.

26. The method of claim 20, wherein the nucleotide sequence comprises bases 2 to 484 of SEQ ID NO:5.

27. The method of claim 20, wherein the protein has at least about 50% identity to the amino acid sequence of SEQ ID NO:3.

28. The method of claim 20, wherein the nucleotide sequence comprises bases 312 to 1055 of SEQ ID NO:6.

29. A plant transformed with a foreign nucleotide sequence encoding a protein that has pathogen resistance activity in the plant, wherein the protein comprises a motif having the amino acid sequence of:

SEQ ID NO:7--X--SEQ ID NO:8--X--SEQ ID NO:9--X--SEQ ID NO:10--X--SEQ ID NO:11, wherein "--X--" represents from zero to about 15 naturally occurring amino acids.

30. The plant in accordance with claim 29 wherein said plant is transformed with a vector that comprises the foreign nucleotide sequence.

31. The plant in accordance with claim 30 wherein the vector further comprises regulatory elements flanking and operably linked to the nucleotide sequence, the regulatory elements controlling expression of the sequence in the plant.

32. The plant according to claim 29, the plant being selected from the group consisting of a monocot and a dicot.

33. The plant according to claim 29 wherein the protein has at least about 50% identity to the protein of SEQ ID NO:1, SEQ ID NO:2 or SEQ ID NO:3 and has pathogen resistance activity.

34. The plant in accordance with claim 29 wherein the protein comprises an amino acid sequence selected from the group consisting of:

(I) the amino acid sequence of SEQ ID NO:1, (ii) the amino acid sequence of SEQ ID NO:2, and (iii) the amino acid sequence of SEQ ID NO:3.

35. The plant according to claim 29 wherein the nucleotide sequence comprises a sequence selected from the group consisting of:

(i) bases 35 to 736 of SEQ ID NO:4, (ii) bases 2 to 484 of SEQ ID NO:5, and (iii) bases 312 to 1055 of SEQ ID NO:6.

36. A progeny plant of the plant of claim 30, wherein the progeny plant comprises the foreign nucleotide sequence.

37. A method for producing a transformed plant having an enhance ability to resist pathogens compared to a nontransformed plant, comprising:

providing a vector comprising a nucleotide sequence encoding a protein, and regulatory elements flanking and operably linked to the nucleotide sequence, the regulatory elements controlling expression of the protein in a plant; and transforming a target plant with the vector to provide a transformed plant, wherein the transformed plant expresses the protein, and wherein the protein comprises a motif having the amino acid sequence of:

SEQ ID NO:7--X--SEQ ID NO:8--X--SEQ ID NO:9--X--SEQ ID NO:10--X--SEQ ID NO:11, wherein "--X--" represents from zero to about 15 naturally occurring amino acids.

38. The method according to claim 37, wherein the target plant is selected from the group consisting of a monocot and and a dicot.

39. The method according to claim 37, wherein the protein has at least about 50% identity to the protein of SEQ ID NO:1, SEQ ID NO:2 or SEQ ID NO:3 and has the pathogen resistance activity thereof.

40. The method according to claim 37, wherein the regulatory elements comprise a plant promoter.

41. A transformed plant obtained according to the method of claim 37.

42. A progeny plant of the plant of claim 41, wherein the progeny plant comprises the nucleotide sequence.

* * * * *

SEQUENCE LISTING

<160> NUMBER OF SEQ ID NOS: 30

<210> SEQ ID NO 1
<211> LENGTH: 231
<212> TYPE: PRT

-continued

```
<213> ORGANISM: Lycopersicon esculentum

<400> SEQUENCE: 1

Met Asp Gln Gln Leu Pro Pro Thr Asn Phe Pro Val Asp Phe Pro Val
1               5                   10                  15

Tyr Arg Arg Asn Ser Ser Phe Ser Arg Leu Ile Pro Cys Leu Thr Glu
            20                  25                  30

Lys Trp Gly Asp Leu Pro Leu Lys Val Asp Asp Ser Glu Asp Met Val
        35                  40                  45

Ile Tyr Gly Leu Leu Lys Asp Ala Leu Ser Val Gly Trp Ser Pro Phe
50                  55                  60

Asn Phe Thr Ala Gly Glu Val Lys Ser Glu Pro Arg Glu Glu Ile Glu
65                  70                  75                  80

Ser Ser Pro Glu Phe Ser Pro Ser Pro Ala Gly Thr Thr Ala Ala Pro
                85                  90                  95

Ala Ala Glu Thr Pro Lys Arg Arg His Tyr Arg Gly Val Arg Gln Arg
            100                 105                 110

Pro Trp Gly Lys Phe Ala Ala Glu Ile Arg Asp Pro Ala Lys Asn Gly
        115                 120                 125

Ala Arg Val Trp Leu Gly Thr Tyr Glu Thr Ala Glu Glu Ala Ala Ile
130                 135                 140

Ala Tyr Asp Lys Ala Ala Tyr Arg Met Arg Gly Ser Lys Ala His Leu
145                 150                 155                 160

Asn Phe Pro His Arg Ile Gly Leu Asn Glu Pro Glu Pro Phe Glu Leu
                165                 170                 175

Arg Arg Lys Gly Arg Ala Ile Gln Gly Pro Ala Ser Ser Ser Gly Asn
            180                 185                 190

Gly Ser Met Lys Arg Arg Lys Ala Val Gln Lys Cys Asp Gly Glu
        195                 200                 205

Met Ala Ser Arg Ser Ser Val Met Gln Val Gly Cys Gln Ile Glu Gln
            210                 215                 220

Leu Thr Gly Val His Gln Leu
225                 230

<210> SEQ ID NO 2
<211> LENGTH: 161
<212> TYPE: PRT
<213> ORGANISM: Lycopersicon esculentum

<400> SEQUENCE: 2

Leu Val Pro Thr Pro Gln Ser Asp Leu Pro Leu Asn Glu Asn Asp Ser
1               5                   10                  15

Gln Glu Met Val Leu Tyr Glu Val Leu Asn Glu Ala Asn Ala Leu Asn
            20                  25                  30

Ile Pro Tyr Leu Pro Gln Arg Asn Gln Leu Leu Pro Arg Asn Asn Ile
        35                  40                  45

Leu Arg Pro Leu Gln Cys Ile Gly Lys Lys Tyr Arg Gly Val Arg Arg
50                  55                  60

Arg Pro Trp Gly Lys Tyr Ala Ala Glu Ile Arg Asp Ser Ala Arg His
65                  70                  75                  80

Gly Ala Arg Val Trp Leu Gly Thr Phe Glu Thr Ala Glu Glu Ala Ala
                85                  90                  95

Leu Ala Tyr Asp Arg Ala Ala Phe Arg Met Arg Gly Ala Lys Ala Leu
            100                 105                 110

Leu Asn Phe Pro Ser Glu Ile Val Asn Ala Ser Val Ser Val Asp Lys
```

```
                115                 120                 125
Leu Ser Leu Cys Ser Asn Ser Tyr Thr Thr Asn Asn Asn Ser Asp Ser
    130                 135                 140

Ser Leu Asn Glu Val Ser Ser Gly Thr Asn Asp Val Phe Glu Ser Arg
145                 150                 155                 160

Cys

<210> SEQ ID NO 3
<211> LENGTH: 248
<212> TYPE: PRT
<213> ORGANISM: Lycopersicon esculentum

<400> SEQUENCE: 3

Met Thr Glu Asn Ser Val Pro Val Ile Lys Phe Thr Gln His Ile Val
1               5                  10                  15

Thr Thr Asn Lys His Val Phe Ser Glu His Asn Glu Lys Ser Asn Ser
            20                  25                  30

Glu Leu Gln Arg Val Val Arg Ile Ile Leu Thr Asp Ala Asp Ala Thr
        35                  40                  45

Asp Ser Ser Asp Asp Glu Gly Arg Asn Thr Val Arg Arg Val Lys Arg
    50                  55                  60

His Val Thr Glu Ile Asn Leu Met Pro Ser Thr Lys Ser Ile Gly Asp
65                  70                  75                  80

Arg Lys Arg Arg Ser Val Ser Pro Asp Ser Asp Val Thr Arg Arg Lys
                85                  90                  95

Lys Phe Arg Gly Val Arg Gln Arg Pro Trp Gly Arg Trp Ala Ala Glu
            100                 105                 110

Ile Arg Asp Pro Thr Arg Gly Lys Arg Val Trp Leu Gly Thr Tyr Asp
        115                 120                 125

Thr Pro Glu Glu Ala Ala Val Val Tyr Asp Lys Ala Ala Val Lys Leu
    130                 135                 140

Lys Gly Pro Asp Ala Val Thr Asn Phe Pro Val Ser Thr Thr Ala Glu
145                 150                 155                 160

Val Thr Val Thr Val Thr Glu Thr Glu Thr Glu Ser Val Ala Asp Gly
                165                 170                 175

Gly Asp Lys Ser Glu Asn Asp Val Ala Leu Ser Pro Thr Ser Val Leu
            180                 185                 190

Cys Asp Asn Asp Phe Ala Pro Phe Asp Asn Leu Gly Phe Cys Glu Val
        195                 200                 205

Asp Ala Phe Gly Phe Asp Val Asp Ser Leu Phe Arg Leu Pro Asp Phe
    210                 215                 220

Ala Met Thr Glu Lys Tyr Tyr Gly Asp Glu Phe Gly Glu Phe Asp Phe
225                 230                 235                 240

Asp Asp Phe Ala Leu Glu Ala Arg
                245

<210> SEQ ID NO 4
<211> LENGTH: 933
<212> TYPE: DNA
<213> ORGANISM: Lycopersicon esculentum

<400> SEQUENCE: 4
atcactagaa aaaaaacta aaattcaaag cgaa atg gat caa cag tta cca ccg    55
                                    Met Asp Gln Gln Leu Pro Pro
                                    1               5 acg aac ttc ccg gta gat ttt ccg gtg tat cgc gga atc tca agc ttc   103
```

```
Thr Asn Phe Pro Val Asp Phe Pro Val Tyr Arg Arg Asn Ser Ser Phe
         10                  15                  20 agt cgt cta att ccc tgt tta act gaa aaa tgg gga gat tta cca cta      151
Ser Arg Leu Ile Pro Cys Leu Thr Glu Lys Trp Gly Asp Leu Pro Leu
         25                  30                  35 aaa gtc gac gat tcc gaa gat atg gta att tac ggt cta tta aaa gac      199
Lys Val Asp Asp Ser Glu Asp Met Val Ile Tyr Gly Leu Leu Lys Asp
40                  45                  50                  55 gct cta agc gtc gga tgg tcg ccg ttt aat ttc acc gcc ggc gaa gta      247
Ala Leu Ser Val Gly Trp Ser Pro Phe Asn Phe Thr Ala Gly Glu Val
                 60                  65                  70 aaa tcg gag ccg aga gaa gaa att gaa tcg tcg cct gaa ttt tca cct      295
Lys Ser Glu Pro Arg Glu Glu Ile Glu Ser Ser Pro Glu Phe Ser Pro
             75                  80                  85 tct ccg gcg gga acc acg gca gct ccg gcg gct gaa aca ccg aaa aga      343
Ser Pro Ala Gly Thr Thr Ala Ala Pro Ala Ala Glu Thr Pro Lys Arg
         90                  95                 100 aga cat tat aga ggc gtt aga cag cgt ccg tgg ggg aaa ttt gcg gcg      391
Arg His Tyr Arg Gly Val Arg Gln Arg Pro Trp Gly Lys Phe Ala Ala
     105                 110                 115 gag att aga gat ccg gcg aag aac gga gct agg gtt tgg ctt gga acg      439
Glu Ile Arg Asp Pro Ala Lys Asn Gly Ala Arg Val Trp Leu Gly Thr
120                 125                 130                 135 tac gaa aca gct gaa gaa gct gca att gct tat gat aaa gct gct tat      487
Tyr Glu Thr Ala Glu Glu Ala Ala Ile Ala Tyr Asp Lys Ala Ala Tyr
                140                 145                 150 aga atg aga gga tca aaa gca cat ttg aat ttc ccg cac cgg atc ggt      535
Arg Met Arg Gly Ser Lys Ala His Leu Asn Phe Pro His Arg Ile Gly
            155                 160                 165 ttg aat gaa ccg gaa ccg ttc gag tta cgg cga aaa ggt cga gcc atc      583
Leu Asn Glu Pro Glu Pro Phe Glu Leu Arg Arg Lys Gly Arg Ala Ile
        170                 175                 180 caa gga ccg gca agc tcg tcg gga aac ggt tcc atg aaa cgg aga aga      631
Gln Gly Pro Ala Ser Ser Ser Gly Asn Gly Ser Met Lys Arg Arg Arg
    185                 190                 195 aaa gcc gtt cag aaa tgt gat gga gaa atg gcg agt aga tca agt gtc      679
Lys Ala Val Gln Lys Cys Asp Gly Glu Met Ala Ser Arg Ser Ser Val
200                 205                 210                 215 atg caa gtt gga tgt caa att gaa caa ttg aca ggt gtc cat caa cta      727
Met Gln Val Gly Cys Gln Ile Glu Gln Leu Thr Gly Val His Gln Leu
                220                 225                 230 ttg gtc att taaaagccga atatttctcc gaacgcaaaa tactatatta              776
Leu Val Ile tttttccaaa tttattgtaa atacgtaata ctctatgata acggagaaaa tagaaagttg    836
aattggaaaa atattgtgat agggttaatc caaagttgta aaagtttca ttttcattaa     896 tattaattta cgtaaaaaaa aaaaaaaaaa aaaaaaa                             933

<210> SEQ ID NO 5
<211> LENGTH: 761
<212> TYPE: DNA
<213> ORGANISM: Lycopersicon esculentum

<400> SEQUENCE: 5 t ctg gtt cca act cct caa agt gat tta cct ctt aat gag aat gac tca    49
  Leu Val Pro Thr Pro Gln Ser Asp Leu Pro Leu Asn Glu Asn Asp Ser
  1               5                  10                  15 caa gag atg gta tta tat gaa gtt ctt aat gaa gct aat gct cta aat      97
Gln Glu Met Val Leu Tyr Glu Val Leu Asn Glu Ala Asn Ala Leu Asn
         20                  25                  30
```

```
att cct tat tta ccc caa cga aat caa tta ctc cct aga aat aat att     145
Ile Pro Tyr Leu Pro Gln Arg Asn Gln Leu Leu Pro Arg Asn Asn Ile
         35                  40                  45 ctt cgt cca tta cag tgc ata ggc aag aaa tac aga gga gta cga cgt     193
Leu Arg Pro Leu Gln Cys Ile Gly Lys Lys Tyr Arg Gly Val Arg Arg
 50                  55                  60 cgt ccg tgg ggg aaa tac gct gcg gaa att cgc gat tcg gct aga cat     241
Arg Pro Trp Gly Lys Tyr Ala Ala Glu Ile Arg Asp Ser Ala Arg His
 65                  70                  75                  80 ggt gcg aga gta tgg cta ggt acg ttc gaa act gct gaa gaa gct gcg     289
Gly Ala Arg Val Trp Leu Gly Thr Phe Glu Thr Ala Glu Glu Ala Ala
                 85                  90                  95 tta gct tat gat aga gcg gct ttt aga atg cga ggt gct aag gca cta     337
Leu Ala Tyr Asp Arg Ala Ala Phe Arg Met Arg Gly Ala Lys Ala Leu
            100                 105                 110 ctt aat ttt cca tct gaa ata gtg aac gcc tct gtt tca gta gac aaa     385
Leu Asn Phe Pro Ser Glu Ile Val Asn Ala Ser Val Ser Val Asp Lys
        115                 120                 125 tta agt ttg tgc tca aat agt tac act acg aat aat aat tca gat tca     433
Leu Ser Leu Cys Ser Asn Ser Tyr Thr Thr Asn Asn Asn Ser Asp Ser
    130                 135                 140 agt tta aat gaa gtt tca agt gga act aat gat gta ttt gaa tca aga     481
Ser Leu Asn Glu Val Ser Ser Gly Thr Asn Asp Val Phe Glu Ser Arg
145                 150                 155                 160 tgt taaaacagag ctgtgcatgg agaatttctt ggcactctaa gcgaataatg          534
Cys tgtggacacg tagaaaatat ttctatttat gtaagaatca actgaactat taaaatttcg   594
ttgttgtatt tatattatgt gcttgcctct tctcttattt tccttatgga attgtttgca   654
gcgacgcacg ctataatctc atgtaaaaag attgcttagg atactttagt agtatgttta   714
taagttgtaa tatacaccdt ctattttcta aaaaaaaaa aaaaaaa                  761

<210> SEQ ID NO 6
<211> LENGTH: 1405
<212> TYPE: DNA
<213> ORGANISM: Lycopersicon esculentum

<400> SEQUENCE: 6
tttggcttta tacctctaat tatattgttc taattatatg gtagaaagat ctacttcccg    60
ccaaaaacaa caaagaaagt aatctctttt tctttgttca ctcatcaact tgtttctcaa   120
atcatttgta tcactgcaac ttttccaca cttaaaaact ttttatacaa taatattggt    180
cactattcac tcacttcaac cagttcttga ttgttttagt actccttttt gagcttatga   240 tgatttttt ttgtgctctt tgaaaaaaat atcttttaaa tcgaactgta actttaagtt   300
tttggtatac c                                                       311 atg acg gaa aat tca gtt ccg gtg att aaa ttc act caa cac ata gta     359
Met Thr Glu Asn Ser Val Pro Val Ile Lys Phe Thr Gln His Ile Val
              5                  10                  15 act aca aac aag cat gtt ttt tct gag cat aac gaa aaa tcc aat tca     407
Thr Thr Asn Lys His Val Phe Ser Glu His Asn Glu Lys Ser Asn Ser
         20                  25                  30 gag tta caa aga gtt gtg agg att ata ctt aca gat gcc gat gct aca     455
Glu Leu Gln Arg Val Val Arg Ile Ile Leu Thr Asp Ala Asp Ala Thr
     35                  40                  45 gat tct tcc gat gat gaa ggc cgg aat act gta cgg aga gtg aag agg     503
Asp Ser Ser Asp Asp Glu Gly Arg Asn Thr Val Arg Arg Val Lys Arg
 50                  55                  60
```

```
cac gtg acg gag atc aac ctt atg ccg tca acc aaa tcg atc ggc gac      551
His Val Thr Glu Ile Asn Leu Met Pro Ser Thr Lys Ser Ile Gly Asp
 65              70                  75                  80 aga aaa cga aga tcg gtg tct ccg gat tct gac gtc act cgt cgg aaa      599
Arg Lys Arg Arg Ser Val Ser Pro Asp Ser Asp Val Thr Arg Arg Lys
                 85                  90                  95 aag ttt aga ggc gtt cgt caa aga ccg tgg ggt cgt tgg gct gca gag      647
Lys Phe Arg Gly Val Arg Gln Arg Pro Trp Gly Arg Trp Ala Ala Glu
            100                 105                 110 att cgg gac ccg acc cgg gga aaa cgg gtg tgg ttg ggt act tat gac      695
Ile Arg Asp Pro Thr Arg Gly Lys Arg Val Trp Leu Gly Thr Tyr Asp
        115                 120                 125 acc cca gaa gaa gca gct gtc gtt tac gat aaa gct gca gtt aag ctc      743
Thr Pro Glu Glu Ala Ala Val Val Tyr Asp Lys Ala Ala Val Lys Leu
    130                 135                 140 aaa ggt cct gac gcc gtt acc aat ttt ccg gta tca aca acg gcg gag      791
Lys Gly Pro Asp Ala Val Thr Asn Phe Pro Val Ser Thr Thr Ala Glu
145                 150                 155                 160 gta acg gtg acg gtt acg gaa acc gaa acc gag tct gtt gcc gac ggt      839
Val Thr Val Thr Val Thr Glu Thr Glu Thr Glu Ser Val Ala Asp Gly
                165                 170                 175 gga gat aaa agc gaa aac gat gtc gct ttg tca ccc acc tca gtt ctc      887
Gly Asp Lys Ser Glu Asn Asp Val Ala Leu Ser Pro Thr Ser Val Leu
            180                 185                 190 tgt gac aat gat ttt gcg ccg ttt gac aat cta ggg ttc tgc gaa gtg      935
Cys Asp Asn Asp Phe Ala Pro Phe Asp Asn Leu Gly Phe Cys Glu Val
        195                 200                 205 gat gct ttt ggt ttc gac gtt gat tca ctt ttc cgg ctg ccg gat ttt      983
Asp Ala Phe Gly Phe Asp Val Asp Ser Leu Phe Arg Leu Pro Asp Phe
    210                 215                 220 gct atg acg gag aaa tac tac ggc gat gaa ttc ggc gaa ttt gac ttt     1031
Ala Met Thr Glu Lys Tyr Tyr Gly Asp Glu Phe Gly Glu Phe Asp Phe
225                 230                 235                 240 gac gat ttt gcc ctt gaa gct cga                                      1055
Asp Asp Phe Ala Leu Glu Ala Arg
                245 tagtgtacga ggggctattt cgtccatttt tgcaaatggg ttcactggtt agttgactag    1115 tgacgtggca ttttggcgg gaatatatat atagtgatta gcagtctcta ttcatacgaa    1175 gactttgtga gagattttg tttttatttt tctgttaatt gtgggtgaat attgtaatat    1235 gaaaatttt gtatggtgaa attgaattaa ttaacgatga agataaggag agtgaagggg    1295 gatgtgtgta ttttatgatt gaggtgtgtt tttgtgattc tgaaaaaata atttattatt    1355 ttacgttgga aatataaagt caaaattcta ttgaaaaaaa aaaaaaaaaa               1405
```

<210> SEQ ID NO 7
<211> LENGTH: 22
<212> TYPE: PRT
<213> ORGANISM: Lycopersicon esculentum
<220> FEATURE:
<221> NAME/KEY: VARIANT
<222> LOCATION: Position 1, 2, 7, 12, 13, 20, 21 and 22
<223> OTHER INFORMATION: amino acids represented by Xaa may be: position
      1, one of His or
<223> OTHER INFORMATION: Lys; position 2, one of Tyr or Phe; position 7,
      one of Gln or
<223> OTHER INFORMATION: Arg; position 12, one of Lys or Arg; position
      13, one of Phe,
<223> OTHER INFORMATION: Tyr or Trp; position 20, one of Pro or Ser;
      position 21, one
<223> OTHER INFORMATION: of Ala or Thr.
<222> LOCATION: Position 22

-continued

```
<223> OTHER INFORMATION: the amino acid represented by Xaa at position
      22 may be one of
<223> OTHER INFORMATION: Lys or Arg.

<400> SEQUENCE: 7

Xaa Xaa Arg Gly Val Arg Xaa Arg Pro Trp Gly Xaa Xaa Ala Ala Glu
1               5                   10                  15

Ile Arg Asp Xaa Xaa Xaa
            20

<210> SEQ ID NO 8
<211> LENGTH: 16
<212> TYPE: PRT
<213> ORGANISM: Lycopersicon esculentum
<220> FEATURE:
<221> NAME/KEY: VARIANT
<222> LOCATION: Position 2, 9, 10, and 12
<223> OTHER INFORMATION: amino acids represented by Xaa may be: position
      2, one of Ala or
<223> OTHER INFORMATION: Lys; position 9, one of Tyr or Phe; position
      10, one of Glu or
<223> OTHER INFORMATION: Asp; position 12, one of Ala or Pro.

<400> SEQUENCE: 8

Gly Xaa Arg Val Trp Leu Gly Thr Xaa Xaa Thr Xaa Glu Glu Ala Ala
1               5                   10                  15

<210> SEQ ID NO 9
<211> LENGTH: 6
<212> TYPE: PRT
<213> ORGANISM: Lycopersicon esculentum
<220> FEATURE:
<221> NAME/KEY: VARIANT
<222> LOCATION: Positions 1 and 4
<223> OTHER INFORMATION: amino acids represented by Xaa may be: position
      1, one of Ala or
<223> OTHER INFORMATION: Val; position 4, one of Lys or Arg.

<400> SEQUENCE: 9

Xaa Tyr Asp Xaa Ala Ala
1               5

<210> SEQ ID NO 10
<211> LENGTH: 7
<212> TYPE: PRT
<213> ORGANISM: Lycopersicon esculentum
<220> FEATURE:
<221> NAME/KEY: VARIANT
<222> LOCATION: Positions 1, 2, 3, 5 and 6
<223> OTHER INFORMATION: amino acids represented by Xaa may be: position
      1, one of Arg or
<223> OTHER INFORMATION: Lys; position 2, one of Met or Leu; position 3,
      one of Arg or
<223> OTHER INFORMATION: Lys; position 5, one of Ser Ala or Pro;
      position 6, one of Lys
<223> OTHER INFORMATION: or Asp.

<400> SEQUENCE: 10

Xaa Xaa Xaa Gly Xaa Xaa Ala
1               5

<210> SEQ ID NO 11
<211> LENGTH: 4
<212> TYPE: PRT
<213> ORGANISM: Lycopersicon esculentum
<220> FEATURE:
<221> NAME/KEY: VARIANT
<222> LOCATION: Position 1
<223> OTHER INFORMATION: amino acids represented by Xaa at position 1
      may be one of Leu
```

```
<223> OTHER INFORMATION: or Thr.

<400> SEQUENCE: 11

Xaa Asn Phe Pro
1

<210> SEQ ID NO 12
<211> LENGTH: 4
<212> TYPE: PRT
<213> ORGANISM: Lycopersicon esculentum
<220> FEATURE:
<223> OTHER INFORMATION: Amino Acids 36-39 of SEQ ID NO:1 and SEQ ID
      NO:4; amino acids
<223> OTHER INFORMATION: 8-11 of SEQ ID NO:2.

<400> SEQUENCE: 12

Asp Leu Pro Leu
1

<210> SEQ ID NO 13
<211> LENGTH: 3
<212> TYPE: PRT
<213> ORGANISM: Lycopersicon esculentum
<220> FEATURE:
<221> NAME/KEY: VARIANT
<222> LOCATION: Positions 1 and 3
<223> OTHER INFORMATION: amino acids represented by Xaa may be: position
      1, one of Asp or
<223> OTHER INFORMATION: Asn; position 3, one of Glu or Gln.

<400> SEQUENCE: 13

Xaa Ser Xaa
1

<210> SEQ ID NO 14
<211> LENGTH: 4
<212> TYPE: PRT
<213> ORGANISM: Lycopersicon esculentum
<220> FEATURE:
<221> NAME/KEY: VARIANT
<222> LOCATION: Position 3
<223> OTHER INFORMATION: amino acids represented by Xaa at position 3
      may be one of Ile,
<223> OTHER INFORMATION: Leu or Val.

<400> SEQUENCE: 14

Met Val Xaa Tyr
1

<210> SEQ ID NO 15
<211> LENGTH: 24
<212> TYPE: DNA
<213> ORGANISM: Artificial Sequence
<220> FEATURE:
<221> NAME/KEY: misc_feature
<222> LOCATION: 1-24
<223> OTHER INFORMATION: primer for PCR reaction of Example 3;
      nucleotides 3-8 represent an
<223> OTHER INFORMATION: Eco RI recognition sequence, nucleotides 9-24
      represent
<223> OTHER INFORMATION: nucleotides 312-327 of SEQ ID NO:6 and the
      first two nucleotides
<223> OTHER INFORMATION: are used to increase binding of Eco RI to its
      recognition sequence.

<400> SEQUENCE: 15
gagaattcat gacggaaaat tcag                                          24

<210> SEQ ID NO 16
```

```
<210> SEQ ID NO 16
<211> LENGTH: 17
<212> TYPE: DNA
<213> ORGANISM: Artificial Sequence
<220> FEATURE:
<221> NAME/KEY: misc_feature
<222> LOCATION: 1-17
<223> OTHER INFORMATION: T7 primer for PCR reaction of Example 3;
      represents a nucleotide
<223> OTHER INFORMATION: sequence in plasmid pBluescript SK (-).

<400> SEQUENCE: 16
aatacgactc actatag                                                   17

<210> SEQ ID NO 17
<211> LENGTH: 47
<212> TYPE: DNA
<213> ORGANISM: Nicotiana tabacum
<220> FEATURE:
<223> OTHER INFORMATION: represents region -1164 to -1118 of the DNA
      encoding wild type gln2 pathogenesis-related protein
      (1,3-B glucanase)

<400> SEQUENCE: 17
cataagagcc gccactaaaa taagaccgat caaataagag ccgccat                  47

<210> SEQ ID NO 18
<211> LENGTH: 47
<212> TYPE: DNA
<213> ORGANISM: Nicotiana tabacum
<220> FEATURE:
<221> NAME/KEY: mutation
<222> LOCATION: nucleotides 8, 11, 40 and 43.
<223> OTHER INFORMATION: same as sequence in SEQ ID NO:18 except
      nucleotides 8, 11, 40
<223> OTHER INFORMATION: and 43 were changed from "g" to "t".

<400> SEQUENCE: 18
cataagatcc tccactaaaa taagaccgat caaataagat cctccat                  47

<210> SEQ ID NO 19
<211> LENGTH: 177
<212> TYPE: DNA
<213> ORGANISM: Lycopersicon esculentum

<400> SEQUENCE: 19 cat tat aga ggc gtt aga cag cgt ccg tgg ggg aaa ttt gcg gcg gag      48
His Tyr Arg Gly Val Arg Gln Arg Pro Trp Gly Lys Phe Ala Ala Glu
1               5                   10                  15 att aga gat ccg gcg aag aac gga gct agg gtt tgg ctt gga acg tac      96
Ile Arg Asp Pro Ala Lys Asn Gly Ala Arg Val Trp Leu Gly Thr Tyr
            20                  25                  30 gaa aca gct gaa gaa gct gca att gct tat gat aaa gct gct tat aga     144
Glu Thr Ala Glu Glu Ala Ala Ile Ala Tyr Asp Lys Ala Ala Tyr Arg
        35                  40                  45 atg aga gga tca aaa gca cat ttg aat ttc ccg                         177
Met Arg Gly Ser Lys Ala His Leu Asn Phe Pro
    50                  55

<210> SEQ ID NO 20
<211> LENGTH: 177
<212> TYPE: DNA
<213> ORGANISM: Lycopersicon esculentum

<400> SEQUENCE: 20 aaa tac aga gga gta cga cgt cgt ccg tgg ggg aaa tac gct gcg gaa      48
Lys Tyr Arg Gly Val Arg Arg Arg Pro Trp Gly Lys Tyr Ala Ala Glu
1               5                   10                  15
```

```
att cgc gat tcg gct aga cat ggt gcg aga gta tgg cta ggt acg ttc    96
Ile Arg Asp Ser Ala Arg His Gly Ala Arg Val Trp Leu Gly Thr Phe
         20                  25                  30 gaa act gct gaa gaa gct gcg tta gct tat gat aga gcg gct ttt aga   144
Glu Thr Ala Glu Glu Ala Ala Leu Ala Tyr Asp Arg Ala Ala Phe Arg
     35                  40                  45 atg cga ggt gct aag gca cta ctt aat ttt cca                       177
Met Arg Gly Ala Lys Ala Leu Leu Asn Phe Pro
 50                  55

<210> SEQ ID NO 21
<211> LENGTH: 174
<212> TYPE: DNA
<213> ORGANISM: Lycopersicon esculentum

<400> SEQUENCE: 21 aag ttt aga ggc gtt cgt caa aga ccg tgg ggt cgt tgg gct gca gag    48
Lys Phe Arg Gly Val Arg Gln Arg Pro Trp Gly Arg Trp Ala Ala Glu
         100                 105                 110 att cgg gac ccg acc cgg gga aaa cgg gtg tgg ttg ggt act tat gac    96
Ile Arg Asp Pro Thr Arg Gly Lys Arg Val Trp Leu Gly Thr Tyr Asp
         115                 120                 125 acc cca gaa gaa gca gct gtc gtt tac gat aaa gct gca gtt aag ctc   144
Thr Pro Glu Glu Ala Ala Val Val Tyr Asp Lys Ala Ala Val Lys Leu
     130                 135                 140 aaa ggt cct gac gcc gtt acc aat ttt ccg                           174
Lys Gly Pro Asp Ala Val Thr Asn Phe Pro
145                 150

<210> SEQ ID NO 22
<211> LENGTH: 66
<212> TYPE: DNA
<213> ORGANISM: Lycopersicon esculentum

<400> SEQUENCE: 22 gat tta cca cta aaa gtc gac gat tcc gaa gat atg gta att tac ggt    48
Asp Leu Pro Leu Lys Val Asp Asp Ser Glu Asp Met Val Ile Tyr Gly
1               5                   10                  15 cta tta aaa gac gct cta                                            66
Leu Leu Lys Asp Ala Leu
             20

<210> SEQ ID NO 23
<211> LENGTH: 72
<212> TYPE: DNA
<213> ORGANISM: Lycopersicon esculentum

<400> SEQUENCE: 23 gat tta cct ctt aat gag aat gac tca caa gag atg gta tta tat gaa    48
Asp Leu Pro Leu Asn Glu Asn Asp Ser Gln Glu Met Val Leu Tyr Glu
1               5                   10                  15 gtt ctt aat gaa gct aat gct cta                                    72
Val Leu Asn Glu Ala Asn Ala Leu
             20

<210> SEQ ID NO 24
<211> LENGTH: 102
<212> TYPE: DNA
<213> ORGANISM: Lycopersicon esculentum

<400> SEQUENCE: 24 ata gta act aca aac aag cat gtt ttt tct gag cat aac gaa aaa tcc    48
Ile Val Thr Thr Asn Lys His Val Phe Ser Glu His Asn Glu Lys Ser
```

```
             1               5                  10                 15
aat tca gag tta caa aga gtt gtg agg att ata ctt aca gat gcc gat        96
Asn Ser Glu Leu Gln Arg Val Val Arg Ile Ile Leu Thr Asp Ala Asp
                20                  25                  30 gct aca                                                                102
Ala Thr
```

<210> SEQ ID NO 25
<211> LENGTH: 59
<212> TYPE: PRT
<213> ORGANISM: Lycopersicon esculentum

<400> SEQUENCE: 25

```
His Tyr Arg Gly Val Arg Gln Arg Pro Trp Gly Lys Phe Ala Ala Glu
1               5                  10                  15

Ile Arg Asp Pro Ala Lys Asn Gly Ala Arg Val Trp Leu Gly Thr Tyr
                20                  25                  30

Glu Thr Ala Glu Glu Ala Ala Ile Ala Tyr Asp Lys Ala Ala Tyr Arg
            35                  40                  45

Met Arg Gly Ser Lys Ala His Leu Asn Phe Pro
        50                  55
```

<210> SEQ ID NO 26
<211> LENGTH: 59
<212> TYPE: PRT
<213> ORGANISM: Lycopersicon esculentum

<400> SEQUENCE: 26

```
Lys Tyr Arg Gly Val Arg Arg Arg Pro Trp Gly Lys Tyr Ala Ala Glu
1               5                  10                  15

Ile Arg Asp Ser Ala Arg His Gly Ala Arg Val Trp Leu Gly Thr Phe
                20                  25                  30

Glu Thr Ala Glu Glu Ala Ala Leu Ala Tyr Asp Arg Ala Ala Phe Arg
            35                  40                  45

Met Arg Gly Ala Lys Ala Leu Leu Asn Phe Pro
        50                  55
```

<210> SEQ ID NO 27
<211> LENGTH: 58
<212> TYPE: PRT
<213> ORGANISM: Lycopersicon esculentum

<400> SEQUENCE: 27

```
Lys Phe Arg Gly Val Arg Gln Arg Pro Trp Gly Arg Trp Ala Ala Glu
1               5                  10                  15

Ile Arg Asp Pro Thr Arg Gly Lys Arg Val Trp Leu Gly Thr Tyr Asp
                20                  25                  30

Thr Pro Glu Glu Ala Ala Val Val Tyr Asp Lys Ala Ala Val Lys Leu
            35                  40                  45

Lys Gly Pro Asp Ala Val Thr Asn Phe Pro
        50                  55
```

<210> SEQ ID NO 28
<211> LENGTH: 22
<212> TYPE: PRT
<213> ORGANISM: Lycopersicon esculentum

<400> SEQUENCE: 28

```
Asp Leu Pro Leu Lys Val Asp Asp Ser Glu Asp Met Val Ile Tyr Gly
1               5                  10                  15
```

```
Leu Leu Lys Asp Ala Leu
            20

<210> SEQ ID NO 29
<211> LENGTH: 24
<212> TYPE: PRT
<213> ORGANISM: Lycopersicon esculentum

<400> SEQUENCE: 29

Asp Leu Pro Leu Asn Glu Asn Asp Ser Gln Glu Met Val Leu Tyr Glu
1               5                   10                  15

Val Leu Asn Glu Ala Asn Ala Leu
            20

<210> SEQ ID NO 30
<211> LENGTH: 34
<212> TYPE: PRT
<213> ORGANISM: Lycopersicon esculentum

<400> SEQUENCE: 30

Ile Val Thr Thr Asn Lys His Val Phe Ser Glu His Asn Glu Lys Ser
1               5                   10                  15

Asn Ser Glu Leu Gln Arg Val Val Arg Ile Ile Leu Thr Asp Ala Asp
            20                  25                  30

Ala Thr
```